United States Patent [19]

Kobayashi et al.

[11] Patent Number: 4,693,748

[45] Date of Patent: Sep. 15, 1987

[54] COMPOSITION FOR STAINING MATERIAL

[75] Inventors: Shigeyoshi Kobayashi, Kawasaki; Tsuneo Manabe; Ichiro Yanagisawa, both of Yokohama, all of Japan

[73] Assignee: Asahi Glass Company Ltd., Tokyo, Japan

[21] Appl. No.: 912,514

[22] Filed: Sep. 29, 1986

[51] Int. Cl.[4] .......................... C09K 3/00; A61K 8/00
[52] U.S. Cl. ........................................ 106/35; 106/34; 433/203.1; 501/48
[58] Field of Search ...................... 106/35, 34; 501/48; 433/203.1

[56] References Cited

U.S. PATENT DOCUMENTS

| 4,612,053 | 9/1986 | Brown et al. | 106/35 |
| 4,617,279 | 10/1986 | Manabe | 106/35 |
| 4,626,514 | 12/1986 | Watanabe et al. | 106/35 |

OTHER PUBLICATIONS

Abstract of Japanese Patent 0178802/85, Kyshu Refractories.

*Primary Examiner*—Theodore Morris
*Attorney, Agent, or Firm*—Oblon, Fisher, Spivak, McClelland, & Maier

[57] ABSTRACT

A staining composition for use in manufacturing artificial tooth, etc. which is composed of Ca and P at their atomic ratio (Ca/P) in a range of from 0.05 to 0.33; and 5 to 28 mol % of $Al_2O_3$.

4 Claims, No Drawings

COMPOSITION FOR STAINING MATERIAL

This invention relates to a composition for staining material, and, more particularly, it is concerned with a composition for calcium phosphate type staining material having excellent water-resistant property.

As the material for artificial tooth, there have so far been known and used metals, resins, dental porcelain, and so forth. These materials have their own color which is different from that of the natural tooth, and also do not possess the particular banded patterns as on the surface of the natural tooth. On account of this, there have been proposed various expedients in bringing the outer appearance of these materials closer to that of the natural tooth. One of such expedients is to bake a material for imparting the pattern of the natural tooth, i.e., the staining material on the surface of such artificial tooth materials.

Heretofore, feldspar type or silicate type material has been used as the staining material. These materials require a high baking temperature in a range of from 1,100° C. to 1,200° C. However, the dental material to be coated with the staining material per se becomes disadvantageously discolored or deformed.

Further, while there have been proposed, as the staining material, those which are capable of being baked at a relatively low temperature, they are generally poor in their water-resistant property and durability, hence seldom used in practice.

On the other hand, there has been proposed in recent years calcium phosphate type crystallized glass as the material for the artificial tooth. This material has its composition very close to that of the natural tooth, hence it has such advantage that it is well adaptable to the organism. However, even this material has no external appearance same as that of the natural tooth, hence it is still necessary to adjust its external appearance with use of the staining material.

However, the afore-described staining materials, in general, have poor adaptability to calcium phosphate and dental porcelain.

On the other hand, there has been proposed a calcium phosphate type staining material which is composed of Ca and P at their atomic ratio (Ca/P) in a range of from 0.35 to 1.7; and 0.1 to 30% by weight of $Li_2O$ (vide: Japanese Unexamined Patent Publication No. 178802/1985). While this staining material is capable of decreasing its melting point at the time of the baking process, it has considerably poor water-resistant property and durability, hence the material has its disadvantage of having no practical usefulness.

With a view, therefore, to finding out the staining material which is capable of removing the disadvantages inherent in the conventional staining material, which has high water-resistant property and durability, and yet which is capable of being baked at a relatively low temperature, the present inventors have made various studies and researches, as the result of which they have finally arrived at the present invention.

That is to say, according to the present invention, in general aspect of it, there is provided a composition for a calcium phosphate type staining material which is composed of Ca and P at their atomic ratio (Ca/P) in a range of from 0.05 to 0.33; and 5 to 32 mol % of $Al_2O_3$.

If the Ca/P atomic ratio is below 0.05, it is difficult to obtain a homogeneous molten substance, and the baking temperature becomes too high to be of practical use. On the other hand, if the Ca/P atomic ratio exceeds 0.33, the water-resistant property of the material is practically insufficient, to whatever extent the quantity of alumina ($Al_2O_3$) in the composition may be adjusted.

If the quantity of $Al_2O_3$ is below 5 mol %, the water-resistant property of the material becomes insufficient. On the other hand, if its content exceeds 32 mol %, uniform molten substance is difficult to obtain with the consequence that the baking temperature becomes too high to be of practical use.

Of the above-mentioned compositional ranges, when the staining material is composed of Ca and P at their atomic ratio (Ca/P) in a range of from 0.07 to 0.25; and 13 to 28 mol % of $Al_2O_3$, sufficient water-resistant property and durability are secured, and, at the same time, the baking process can be advantageously carried out at a temperature of 750° C. or in its vicinity.

The staining material according to the present invention may further contain therein a coloring component. Such coloring component has its effect of bringing the color of the staining material closer to that of the natural tooth. Examples of such coloring component are oxides of those metals selected from Ni, Ru, Fe, Mn, W, Ce, Ti, Co, Cr, V, Mo, Rh, Pd, U, Nd and Au. Of these various coloring components, the oxides of Ni and Ru are particularly preferable, since they are capable of developing color which is very close to that of the natural tooth, ranging from light yellow to yellowish brown in tone.

Such coloring component may be added to the staining material in a quantity ranging from 0.02 to 10% by weight relative to the total amount of the composition for the staining material. When the adding quantity is below 0.02% by weight, the coloring effect is not sufficient; and, when it exceeds 10% by weight, the coloring effect becomes excessive to bring about considerable difference from the color of the natural tooth. With the adding quantity of the coloring component ranging from 0.05 to 5% by weight, there can be obtained sufficient and stable coloring effect very close to the color of the natural tooth, the range of which is therefore particularly preferable.

In the production of the staining material according to the present invention, the following substances may be used as the starting materials.

For the calcium material, calcium carbonate and calcium oxide are the most representative, besides which there may be used inorganic salts and organic salts such as calcium hydroxide, calcium oxalate, calcium acetate, and so forth.

For the phosphoric material, there may be used phosphoric acids such as orthophosphoric acid, or ammonium salts of these phosphoric acids. Besides these, there may be used calcium salts of the phosphoric acids such as calcium phosphate, calcium hydrogen phosphate, calcium pyrophosphate, acid calcium phosphate, calcium polyphosphates, hydroxy apatite, and so forth. These calcium salts of phosphoric acid can be used singly or in mixture with other calcium compounds or phosphoric compounds.

For the aluminum material, there may be used, for example, aluminum hydroxide, aluminum oxide, aluminum nitrate, aluminum chloride, aluminum phosphate, and so forth.

With these starting materials, the staining composition of the present invention is produced in the following process steps.

A predetermined amount of the calcium material, the phosphoric material and the aluminum material are prepared and mixed; the mixture is further made into slurry, if desired; then it is dried and thereafter melted at a temperature of from 1,000° C. to 1,500° C. The molten material is taken out to a place maintained at an ambient temperature. The molten material as taken out is cooled down to form a glass block, which is then crushed to a grain size of from 1 to 2 mm in diameter. Subsequently, the crushed material is pulverized in a ball mill into fine powder of the staining material according to the present invention having its specific surface area of 0.5 $m^2/g$ or above. The thus obtained powder of the staining material is made into slurry by addition water. This slurry is then applied onto the surface of the artificial tooth, dried at a temperature of 100° C. or so, and then maintained in an electric furnace for a period of from 5 to 30 minutes at a temperature in a range of from 700° C. to 900° C. In this case, the staining material is applied onto the surface of the artificial tooth in such a manner that it may form the surface pattern of the natural tooth, or simply give the color of the natural tooth.

In the case of adding the coloring component to the staining material according to the present invention, such coloring component is usually mixed with the starting materials for the staining composition at the time of its preparation. However, it may also be possible that the coloring component is added to the pre-mixed powder of the staining material, then it is melted on the surface of the artificial tooth under heat together with the staining material, thereby being mixed with it.

The staining material according to the present invention may further include therein other components such as, for example, a melting point decreasing agent like alkali metal oxides; a color stabilizer like silica; and so forth, so far as addition of these components may not depart from the intended object of the present invention.

In the following, a few preferred examples of the present invention together with a comparative example are presented for more detailed explanation thereof, for its proper practice, and for proving superiority of the staining material according to the present invention to the conventional staining composition.

EXAMPLE 1

$CaCO_3$, $Al(OH)_3$ and $H_3PO_4$, each being in a quantity as determined by calculation so that the final product may contain therein 11 mol % of CaO, 26 mol % of $Al_2O_3$, and 63 mol % of $P_2O_5$, were mixed. The mixture was dried, placed in a platinum crucible, maintained therein at a temperature of 400° C. for five hours, and subsequently maintained in an electric furnace at a temperature of 1,350° C. for one hour to become molten. The molten material was decanted onto a graphite plate, whereby transparent glass (Ca/P=0.09; $Al_2O_3$=21.7% by weight) was obtained. The thus obtained glass was then crushed to an average grain size of 0.6 mm, after which it was pulverized in a ball mill to fine particles of the staining material having its specific surface area of 1.5 $m^2/g$.

To 1 g of this staining powder, there was added 3 g of water, and the mixture was made into slurry. The slurry was applied onto the surface of a crown made of calcium phosphate type crystallized glass, and dried in air. Subsequently, the crown was held in an electric furnace at a temperature of 780° C. for ten minutes. The crown as taken out of the electric furnace had smooth and glazed surface with a colorless transparent coated layer free from irregularity and defects.

This crown was then immersed in water at 80° C. for ten days, after which it was taken out for observation. As the result, there was recognized no exfoliation of, or turbidity in, the coated layer. Dissolved $P_2O_5$ in the immersion solution was 0.30 mg.

EXAMPLE 2

$CaCO_3$, $Al_2O_3$, $H_3PO_4$ and NiO, each being in a quantity as determined by calculation so that the final product may contain therein 12 mol % of CaO, 20 mol % of $Al_2O_3$, 67.8 mol % of $P_2O_5$ and 0.2 mol % of NiO, were mixed. From this mixture, the transparent glass (Ca/P=0.09; $Al_2O_3$=16.5% by weight) was obtained in the same manner as in Example 1 above.

The thus obtained glass was crushed and pulverized in the same manner as in Example 1 above, thereby obtaining the staining powder having the specific surface area of 1.0 $m^2/g$.

To 1 g of this powder, there was added 3 g of water to form a slurry. The slurry was then coated on the surface of a crown made of calcium phosphate type crystallized glass, and dried in air. Subsequently, this crown was maintained for five minutes in an electric furnace at a temperature of 790° C. The crown as taken out of the electric furnace had smooth and glazed surface with a transparent coated layer uniformly tinted in light brown. As the result of the water-resistant test same as Example 1 above, this crown indicated that it had no exfoliation of, or turbidity in, the coated layer. Dissolved $P_2O_5$ in the immersion solution was 0.30 mg.

EXAMPLE 3

$CaCO_3$, $Al(OH)_3$, $H_3PO_4$ and $CeO_2$, each being in a quantity as determined by calculation so that the final product may contain therein 18 mol % of CaO, 15 mol % of $Al_2O_3$, 66 mol % of $P_2O_5$, and 1 mol % of $CeO_2$, were mixed. From this mixture, the transparent glass (Ca/P=0.14; $Al_2O_3$=12.7% by weight) was obtained in the same manner as in Example 1 above.

The thus obtained glass was crushed and pulverized in the same manner as in Example 1 above, thereby obtaining the staining powder having the specific surface area of 1.0 $m^2/g$.

To 1 g of this staining powder, there was added 3 g of water to form a slurry. The slurry was then coated on the surface of a crown made of calcium phosphate type crystallized glass, and dried in air. Subsequently, this crown was maintained in an electric furnace at a temperature of 780° C. for ten minutes. The crown as taken out of the electric furnace had smooth and glazed surface with a transparent coating layer uniformly tinted in light yellowish brown. As the result of the water-resistant test same as Example 1 above, this crown indicated that it had no exfoliation of, or turbidity in, the coated layer. Dissolved $P_2O_5$ in the immersion solution was 0.62 mg.

EXAMPLE 4

$Ca_2H_4(PO_4)_2$, $Al(OH)_3$, $H_3PO_4$ and $CeO_2$, each being in a quantity as determined by calculation so that the final product main contain therein 15 mol % of CaO, 25 mol % of $Al_2O_3$, 59 mol % of $P_2O_5$ and 1 mol % of $CeO_2$, were mixed. From this mixture, the transparent glass (Ca/P=0.13; $Al_2O_3$=21.4% by weight) was obtained in the same manner as in Example 1 above.

The thus obtained glass was crushed and pulverized in the same manner as in Example 1 above, thereby obtaining the staining powder having the specific surface area of 1.0 m²/g.

To 1 g of this staining powder, there was added 3 g of water to form a slurry. The slurry was then coated on the surface of a crown made of calcium phosphate type crystallized glass, and dried in air. Subsequently, this crown was maintained in an electric furnace at a temperature of 800° C. for five minutes. The crown as taken out of the electric furnace had smooth and glazed surface with a transparent coated layer uniformly tinted in light yellow.

As the result of the water-resistant test same as Example 1 above, this crown indicated that it had no exfoliation of, or turbidity in, the coated layer. Dissolved $P_2O_5$ in the immersion solution was 0.40 mg.

COMPARATIVE EXAMPLE $CaCO_3$, $Al(OH)_3$ and $H_3PO_4$, each being in a quantity as determined by calculation so that the final product may contain therein 40 mol % of CaO, 5 mol % of $Al_2O_3$, and 55 mol % of $P_2O_5$, were mixed. From this mixture, the transparent glass (Ca/P=0.36) was obtained in the same manner as in Example 1 above.

The thus obtained glass was crushed and pulverized in the same manner as in Example 1 above, thereby obtaining the staining powder having the specific surface area of 1.5 m²/g.

To 1 g of this staining powder, there was added 3 g of water to form a slurry. The slurry was then coated on the surface of a crown made of calcium phosphate type crystallized glass, and dried in air. Subsequently, this crown was maintained in an electric furnace at a temperature of 780° C. for ten minutes. The crown as taken out of the electric furnace was subjected to the water-resistant test same as in Example 1 above. As the result, it was found that turbidity occurred throughout the coated layer, and that a part of the coated layer had been exfoliated from the surface of the crown, and the other part thereof could be easily peeled off by nail. Dissolved $P_2O_5$ in the immersion solution was 8.87 mg.

We claim:

1. A composition for a calcium phosphate type staining material, which is composed of Ca and P at their atomic ratio (Ca/P) in a range of from 0.05 to 0.33; and 5 to 28 mol % of $Al_2O_3$.

2. The composition according to claim 1, wherein the atomic ratio of Ca to P is in a range of from 0.07 to 0.25, and the content of $Al_2O_3$ is in a range of from 13 to 22 mol %.

3. The composition according to claim 1, further including a coloring component in a range of from 0.02 to 10% by weight relative to the total quantity of said composition.

4. The composition according to claim 3, wherein said coloring component is in a range of from 0.05 to 5% by weight.

* * * * *